United States Patent
Palreddy et al.

(10) Patent No.: US 8,073,532 B2
(45) Date of Patent: Dec. 6, 2011

(54) METHOD AND APPARATUS FOR BEAT ALIGNMENT AND COMPARISON

(75) Inventors: Surekha Palreddy, Maplewood, MN (US); Jay A. Warren, San Juan Capistrano, CA (US); Alan H. Ostroff, San Clemente, CA (US)

(73) Assignee: Cameron Health, Inc., San Clemente, CA (US)

( * ) Notice: Subject to any disclaimer, the term of this patent is extended or adjusted under 35 U.S.C. 154(b) by 145 days.

(21) Appl. No.: 12/353,114

(22) Filed: Jan. 13, 2009

(65) Prior Publication Data

US 2009/0125075 A1 May 14, 2009

Related U.S. Application Data

(63) Continuation of application No. 10/999,274, filed on Nov. 29, 2004, now Pat. No. 7,477,935.

(51) Int. Cl.
*A61N 1/365* (2006.01)

(52) U.S. Cl. .......... 600/518; 607/14; 600/509; 600/510; 128/920

(58) Field of Classification Search .......... 600/509–510, 600/518; 128/920; 607/14
See application file for complete search history.

(56) References Cited

U.S. PATENT DOCUMENTS

| | | | |
|---|---|---|---|
| 4,170,992 A | 10/1979 | Dillman | |
| 5,217,021 A | 6/1993 | Steinhaus et al. | |
| 5,271,411 A | 12/1993 | Ripley et al. | |
| 5,273,049 A | 12/1993 | Steinhaus et al. | |
| 5,431,693 A | 7/1995 | Schroeppel | |
| 5,779,645 A | 7/1998 | Olson et al. | |
| 5,891,047 A | 4/1999 | Lander et al. | |
| 6,266,554 B1 | 7/2001 | Hsu et al. | |
| 6,308,095 B1 | 10/2001 | Hsu et al. | |
| 6,377,844 B1 | 4/2002 | Graen | |
| 6,397,100 B2 | 5/2002 | Stadler et al. | |
| 6,493,579 B1 | 12/2002 | Gilkerson et al. | |
| 6,493,584 B1 | 12/2002 | Lu | |
| 6,567,691 B1 | 5/2003 | Stadler | |
| 6,574,505 B1 | 6/2003 | Warren | |
| 6,625,490 B1 | 9/2003 | McClure et al. | |
| 6,684,100 B1 | 1/2004 | Sweeney et al. | |
| 6,687,540 B2 | 2/2004 | Marcovecchio | |
| 6,708,062 B2 | 3/2004 | Ericksen et al. | |

(Continued)

OTHER PUBLICATIONS

Swerdlow et al.; "Advanced ICD Troubleshooting: Part I"; Pacing and Clinical Electrophysiology; Jan. 9, 2006.

(Continued)

*Primary Examiner* — Carl H Layno
*Assistant Examiner* — Deborah Malamud
(74) *Attorney, Agent, or Firm* — Pramudji Law Group PLLC; Ari Pramudji; Mark Schroeder

(57) ABSTRACT

Methods of using a template having a template data set and template parameters to provide improved alignment of captured cardiac signal data to a stored template. More particularly, in an illustrative method, a captured cardiac signal is first configured using template parameters for a stored template. Then, once configured, the captured cardiac signal is then compared to the stored template. Other embodiments include implantable cardiac treatment devices including operational circuitry configured to perform the illustrative method. In a further embodiment, more than one stored templates may be used. Each template can have independently constructed parameters, such that a single captured cardiac signal may be configured using first parameters for comparison to a first template, and using second parameters for comparison to a second template.

19 Claims, 5 Drawing Sheets

U.S. PATENT DOCUMENTS

| | | | |
|---|---|---|---|
| 6,731,978 | B2 | 5/2004 | Olson et al. |
| 6,745,068 | B2 | 6/2004 | Koyrakh et al. |
| 6,996,434 | B2 | 2/2006 | Marcovecchio et al. |
| 2002/0049474 | A1 | 4/2002 | Marcovecchio et al. |
| 2003/0181818 | A1* | 9/2003 | Kim et al. ............... 600/509 |
| 2004/0176694 | A1 | 9/2004 | Kim et al. |
| 2005/0131478 | A1 | 6/2005 | Kim et al. |

OTHER PUBLICATIONS

Ge, Dingfei et al., "Cardiac Arrhythmia Classification Using Autoregressive Modeling," Biomedical Engineering Online, http://www.biomedical-engineering-online.com, Nov. 13, 2002, 12 pages.

Office Action of Australian Patent Office (Oct. 19, 2010), Amendment (Apr. 15, 2011), and IPAU Allowance (May 4, 2011); from Australian Patent Application No. 2005310007 (claiming same priority benefit as U.S. Appl. No. 12/353,114).

Office Action of European Patent Office (May 8, 2008) and Amendment (Sep. 18, 2009); from European Patent Application 05 810 093.4 (claiming same priority benefit as U.S. Appl. No. 12/353,114).

International Preliminary Report on Patentability (Jun. 7, 2007), PCT/US2005/037760; (claiming same priority benefit as U.S. Appl. No. 12/353,114).

* cited by examiner

METHOD AND APPARATUS FOR BEAT ALIGNMENT AND COMPARISON

RELATED APPLICATIONS

This application is a continuation of U.S. patent application Ser. No. 10/999,274, filed Nov. 29, 2004, now U.S. Pat. No. 7,477,935 and titled METHOD AND APPARATUS FOR BEAT ALIGNMENT AND COMPARISON, the entire disclosure of which is herein incorporated by reference.

The present invention is related to U.S. patent application Ser. No. 10/999,853, filed Nov. 29, 2004, now U.S. Pat. No. 7,376,458 and titled METHOD FOR DEFINING SIGNAL TEMPLATES IN IMPLANTABLE CARDIAC DEVICES, which has a continuation filed as U.S. patent application Ser. No. 11/941,781, on Nov. 16, 2007 and titled METHOD FOR DEFINING SIGNAL TEMPLATES IN IMPLANTABLE CARDIAC DEVICES. The disclosures of these aforementioned applications are incorporated herein by reference.

FIELD

The present invention is related to the field of electrical cardiac treatment and devices. More particularly, the present invention is related to analysis of electrical cardiac signals for diagnostic/therapeutic purposes.

BACKGROUND

Implantable cardiac rhythm management devices are an effective treatment in managing irregular cardiac rhythms in particular patients. Implantable cardiac rhythm management devices are capable of recognizing and treating arrhythmias with a variety of therapies. To effectively deliver these therapies, however, cardiac rhythm management devices must first accurately sense and classify an episode.

In order to apply the proper therapy in responding to an episode, some cardiac rhythm management devices compare sensed cardiac signals to a previously stored "template" representing normal sinus rhythm (NSR) or other "template" frequently intended to represent the patient's NSR. Problems arise when the cardiac rhythm management device inaccurately compares a sensed cardiac complex to a stored NSR template, and as a result, misclassifies the sensed cardiac complex. The severity of this problem escalates if the cardiac rhythm management device inappropriately delivers and/or withholds therapy due to the misclassification. In illustration, when a particular group of sensed complexes are erroneously compared to a stored template because of an improper alignment to the template, a cardiac rhythm management device may mistakenly classify these sensed complexes as a mismatch and even possibly as a tachyarrhythmia.

Much of the analysis performed on cardiac signals includes sampling a cardiac signal and comparing the sampled signal to a stored template. Thus, a series of sampled signals are compared to stored data. Often a correlation analysis is performed to compare the two data sets. Typically, a number of peaks will appear in each signal. If the peaks are poorly aligned, low correlation will often result. With poor alignment, a "good" sampled signal may, in analysis, illustrate poor correlation, erroneously indicating treatment. Techniques for enabling and assuring good alignment are therefore desired.

SUMMARY

The present invention, in an illustrative embodiment, makes use of a template having a template data set and template parameters to provide improved alignment of captured cardiac signal data to a stored template. More particularly, in an illustrative method, a captured cardiac signal is first configured using template parameters for a stored template. Then, once configured, the captured cardiac signal is then compared to the stored template. Other embodiments include implantable cardiac treatment devices including operational circuitry configured to perform the illustrative method.

In a further embodiment, more than one stored templates may be used. Each template can have independently constructed templates, such that a single captured cardiac signal may be configured using first parameters for comparison to a first template, and using second parameters for comparison to a second template.

DETAILED DESCRIPTION

The following detailed description should be read with reference to the drawings. The drawings, which are not necessarily to scale, depict illustrative embodiments and are not intended to limit the scope of the invention. Those skilled in the art will recognize that many of the examples provided have suitable alternatives that may be utilized.

The present invention is generally related to implantable cardiac treatment systems that provide therapy for patients who are experiencing particular arrhythmias. The present invention is directed toward detection architectures for use in cardiac rhythm devices. In particular, the present invention is suited for implantable cardiac treatment systems capable of detecting and treating harmful arrhythmias. Although the detection architecture is intended primarily for use in an implantable medical device that provides defibrillation therapy, the invention is also applicable to cardiac rhythm devices (including external devices) directed toward anti-tachyarrhythmia pacing (ATP) therapy, pacing, and other cardiac rhythm devices capable of performing a combination of therapies to treat rhythm disorders.

To date, implantable cardiac treatment systems have been either epicardial systems or transvenous systems. For example, transvenous systems can be implanted generally as shown in FIG. 1B. However, as further explained herein, the present invention is also adapted to function with a subcutaneous implantable cardiac treatment system as shown in FIG. 1A.

Figure 1A:
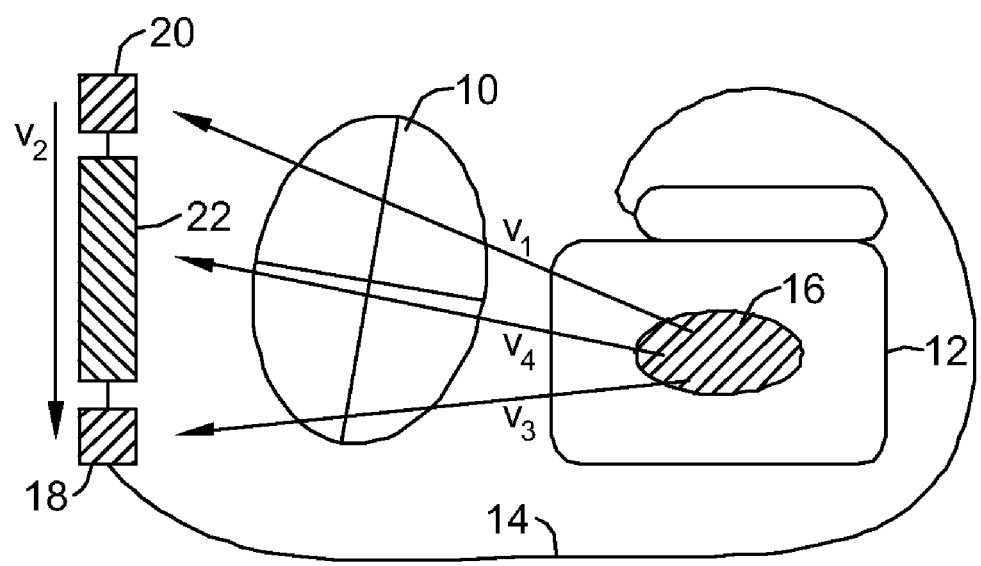
FIGS. 1A-1B illustrate, respectively, representative subcutaneous and intravenous implantable cardiac treatment systems.
Figure 1B:
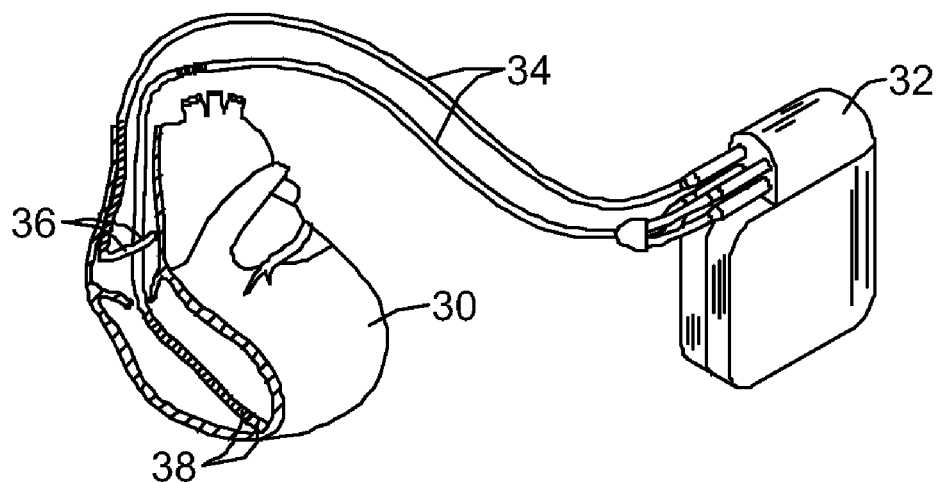

FIG. 1A illustrates a subcutaneously placed implantable cardiac treatment system, in particular, an implantable cardioverter/defibrillator (ICD) system. In this illustrative embodiment, the heart 10 is monitored using a canister 12 coupled to a lead system 14. The canister 12 may include an electrode 16 thereon, while the lead system 14 connects to sensing electrodes 18, 20, and a coil electrode 22 that may serve as a shock or stimulus delivery electrode as well as a sensing electrode. The various electrodes define a number of sensing vectors V1, V2, V3, V4. It can be seen that each vector provides a different vector "view" of the heart's 10 electrical activity. The system may be implanted subcutaneously as illustrated, for example, in U.S. Pat. Nos. 6,647,292 and 6,721,597, the disclosures of which are both incorporated herein by reference. By subcutaneous placement, it is meant that electrode placement does not require insertion of an electrode into a heart chamber, in or on the heart muscle, or the patient's vasculature. In some embodiments, a shock is applied using the canister electrode 12 and one of the lead system electrodes 18, 20, or 22, often the coil electrode 22. In other embodiments, one of the sense electrodes 18, 20 may be used in conjunction with the coil electrode 22 for providing a shock.

FIG. 1B illustrates a transvenous ICD system. The heart 30 is monitored and treated by a system including a canister 32 coupled to a lead system 34 including atrial electrodes 36 and ventricular electrodes 38. A number of configurations for the electrodes may be used, including placement within the heart, adherence to the heart, or disposition within the patient's vasculature.

Figure 2:
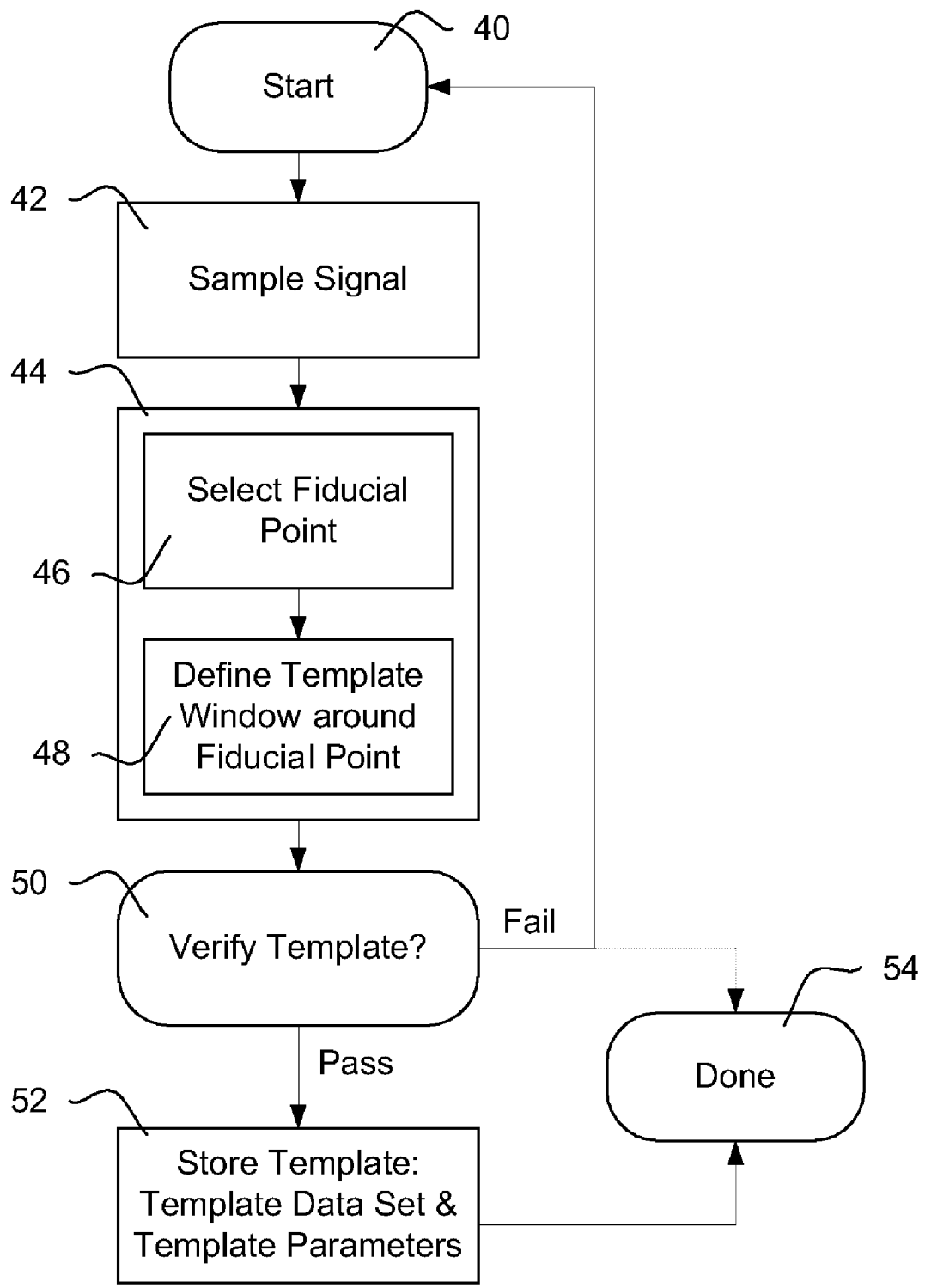
FIG. 2 is a block diagram for an illustrative template formation method.

FIG. 2 is a block diagram for an illustrative template formation method. The illustrative method begins with a start block 40 and has a first step of sampling a signal 42. The signal may be, for example, captured using subcutaneous, transvenous, epicardial, intracardial, or even external electrodes. The illustrative template formation method then defines template parameters 44. Illustratively included in defining the template parameters 44 are the steps of selecting a fiducial point 46 and defining a template window around the fiducial point 48.

With the template parameters defined, and a sample chosen, the next step in the illustrative template formation method is to verify the template 50. This step 50 may include statistical analysis of the template data, comparison of the template to later sampled signals, or other steps that can assure that the template provides an accurate representation of a benign cardiac rhythm. If the template is verified at 50, it passes and is stored as shown at 52. The method of template formation can then be done, as noted at 54. The template is stored both as a template data set and as template parameters. If the template cannot be verified at 50, it fails and the method returns to the start 40. In some embodiments, an attempt to form a template occurs periodically, and if the formation method fails, the method is done 54 until prompted to start again at a later time.

Selecting a fiducial point 46 can be performed in a number of different manners, for example as discussed in U.S. patent application Ser. No. 10/999,853, filed Nov. 29, 2004, now U.S. Pat. No. 7,376,458, and titled METHOD FOR DEFINING SIGNAL TEMPLATES IN IMPLANTABLE CARDIAC DEVICES. For example, a largest positive or negative peak in the signal may be selected. Alternatively, a peak occurring at a particular time (e.g. the first significant peak in the sensed signal) may be selected. In alternative embodiments, a peak or zero in a first or, more likely, second derivative may be selected.

In some methods, the step of setting the template window around the fiducial point 70 is performed by identifying the begin and end of a QRS signal. The observation of monotonic segments may be used to estimate the beginning and end of the QRS segment, as further explained in U.S. patent application Ser. No. 10/999,853, filed Nov. 29, 2004, now U.S. Pat. No. 7,376,458 and titled METHOD FOR DEFINING SIGNAL TEMPLATES IN IMPLANTABLE CARDIAC DEVICES. A monotonic segment is a signal segment of consecutive samples in which the sensed amplitude changes in the same direction or stays the same. For example, a series of consecutive samples in which each successive sample is greater than or equal to (in amplitude) the previous sample would be an increasing monotonic segment. Similarly, a series of consecutive samples in which each successive sample is less than or equal to (in amplitude) the previous sample would be a decreasing monotonic segment. One method for observing monotonic segments is by determining the zero crossing points of the first derivative of the cardiac complex signal. The largest monotonic segment in the sensed signal occurring before the fiducial point may be presumed to represent the start of the QRS complex, while the largest monotonic segment occurring after the fiducial point can then be presumed to represent the end of the QRS complex. One, two, or another number of sample points may be observed beyond these begin and end points for retention in the template window.

For another example, given an isoelectric line in the sensed signal, the number of crossings of the isoelectric line may be noted. Consecutive crossings occurring at intervals of at least a minimum amount may indicate Q-R and R-S intervals, such that the QRS signal can be identified as including the consecutive crossings plus data samples going back and forward a predefined number of samples, such as three samples.

The method shown in FIG. 2 is merely illustrative of one form of template formation. For the present invention, it is sufficient that a tailored template having a template data set and template parameters is or has been formed. Once formed, the template can then be used as further illustrated below.

Figure 3:
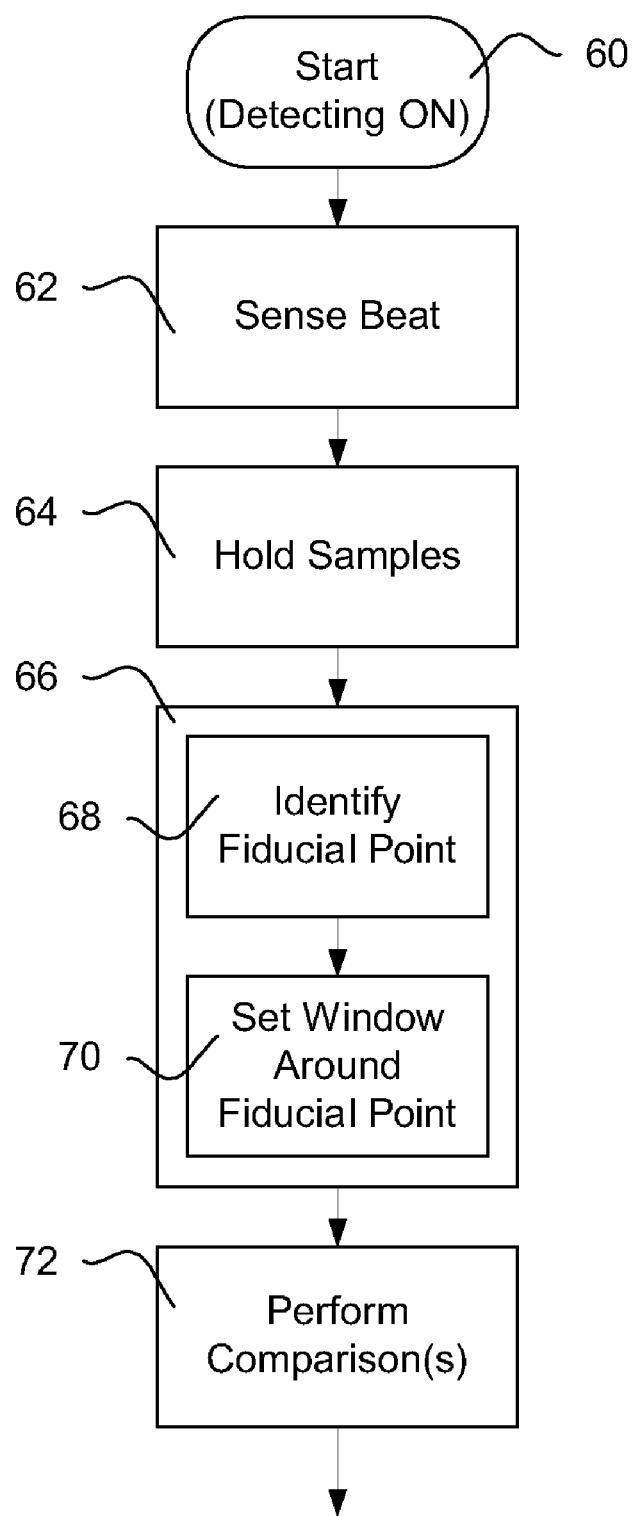
FIG. 3 is a block diagram for an illustrative embodiment.

FIG. 3 is a block diagram for an illustrative embodiment. The method starts 60 with detecting ON such that cardiac signals are being monitored. When a beat (or other event) is sensed, as shown at 62, the method then includes holding a number of samples 64 of the monitored cardiac signal. The beat (or other event) may be sensed in any suitable fashion. If desired, the methods of U.S. patent application Ser. No. 10/858,598, filed Jun. 1, 2004, now U.S. Pat. No. 7,248,598, and titled METHOD AND DEVICES FOR PERFORMING CARDIAC WAVEFORM APPRAISAL, may be used to verify whether the sensed signal likely corresponds to a cardiac event and/or a ventricular event. The disclosure of U.S. patent application Ser. No. 10/858,598 is incorporated herein by reference. If the sensed signal does likely correspond to such an event, the signal may be selected for further analysis.

Next, in accordance with predefined template parameters, the template window is defined at 66. The template window definition may include identifying a fiducial point 68 and setting a window around the fiducial point 70. Next, a comparison is performed 72. The results of the comparison can be used in a variety of manners. Correlation Waveform Analysis is one type of comparison that can be performed. Illustrative types and uses of the comparison are shown in U.S. patent application Ser. No. 10/856,084, filed May 27, 2004, now U.S. Pat. No. 7,330,757, and titled METHOD FOR DISCRIMINATING BETWEEN VENTRICULAR AND SUPRAVENTRICULAR ARRHYTHMIAS, the disclosure of which is incorporated herein by reference. Other conventional comparisons and uses thereof may be utilized here as well.

Figure 4A:
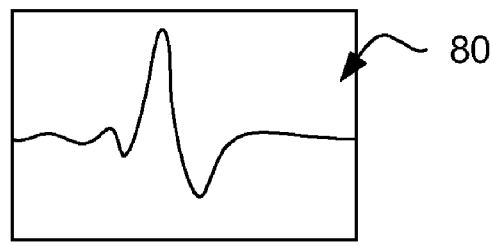
FIGS. 4A-4E show, graphically, an illustrative method for capture, alignment, and comparison of a cardiac signal.
Figure 4B:
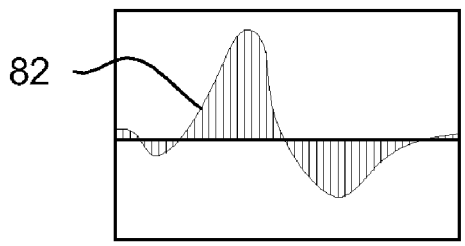
Figure 4C:
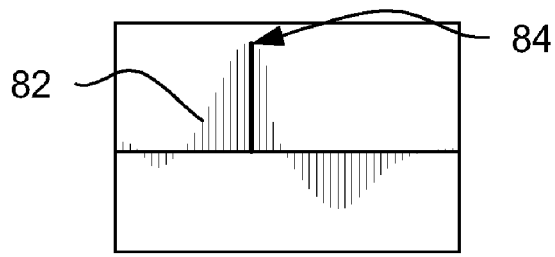
Figure 4D:
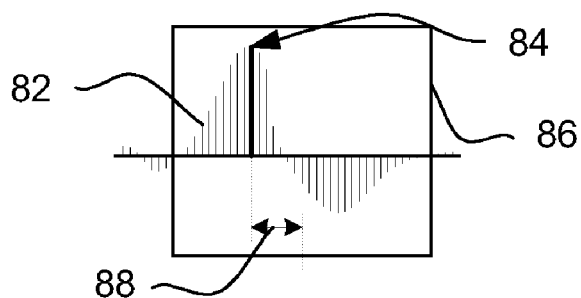

FIGS. 4A-4E show, graphically, an illustrative method for capture, alignment, and comparison of a cardiac signal to a template. FIG. 4A illustrates a sensed signal 80 which can be detected as being a beat. As shown in FIG. 4B, a number of samples 82 are used to discretely capture the beat. FIG. 4C shows that, from the samples 82, a fiducial point 84 has been selected as the peak of the highest positive excursion of the signal from an isoelectric line. FIG. 4D illustrates the windowing of the samples 82, with a window 86 defined around the fiducial point 84. Because the signal has a relatively large trailing portion, the fiducial point 84 is displaced from the center of the window 86 by an offset 88. The steps of selecting a fiducial point and defining the window (as well as the offset) therearound are performed using template parameters defined while forming the template itself.

Figure 4E:
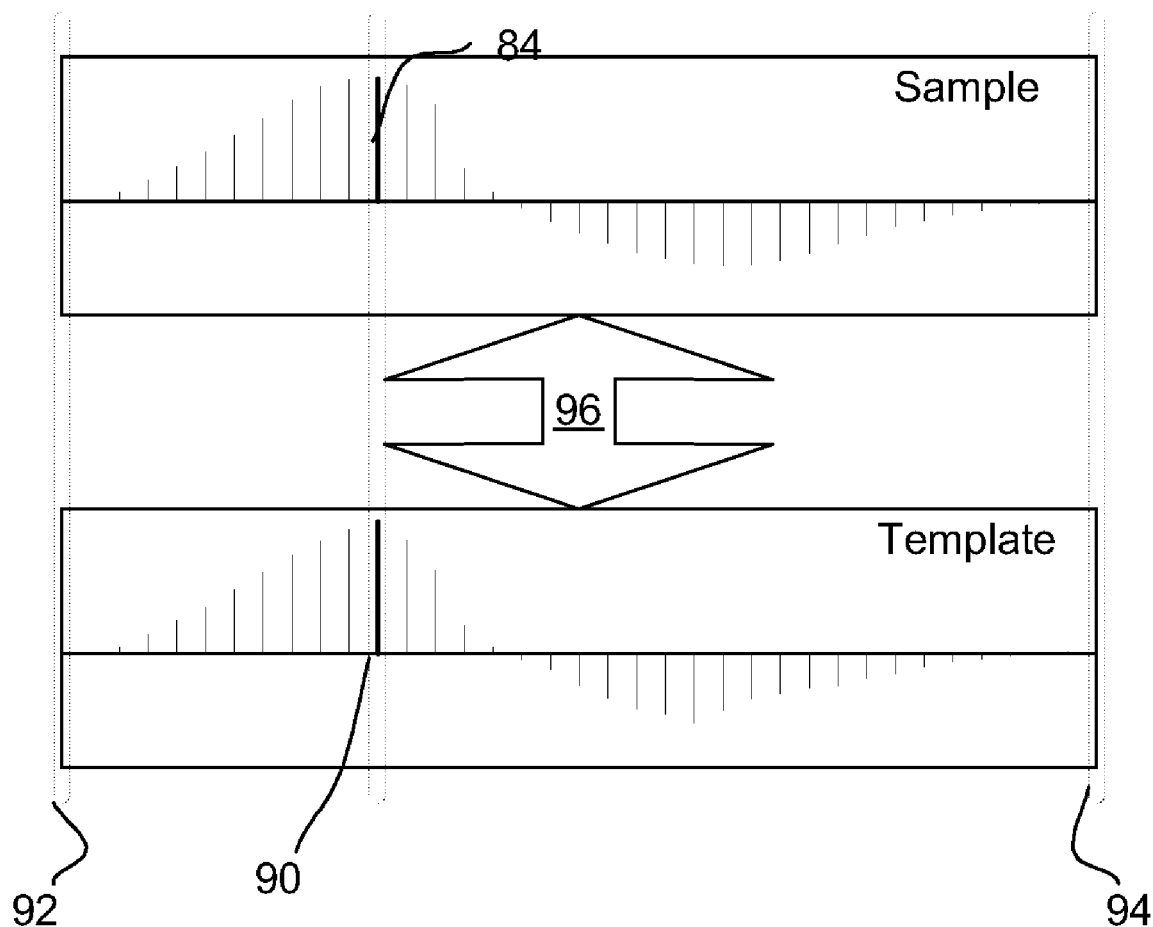

Next, as shown in FIG. 4E, the sample is aligned with the template. More specifically, the sample fiducial point 84 is aligned with the template fiducial point 90. The leading edge 92 and trailing edge 94 of the template and sample windows are then aligned. A comparison 96 can then be performed. By not only aligning the fiducial points 84, 90, but also reconfiguring the sample window and matching the sample window to that used to generate the template, the method advantageously focuses the comparison 96 on the most relevant and useful data available.

The present invention, in some embodiments, is also embodied in devices using operational circuitry including select electrical components provided within the canister 12 (FIG. 1A) or canister 32 (FIG. 1B). In such embodiments, the operational circuitry may be configured to enable the above methods to be performed. In some similar embodiments, the present invention may be embodied in readable instruction sets such as a program encoded in machine or controller readable media, wherein the readable instruction sets are provided to enable the operational circuitry to perform the analysis discussed in the above embodiments. Further embodiments may include a controller or microcontroller adapted to read and execute the above methods. These various embodiments may incorporate the illustrative methods shown in FIGS. 2, 3 and 4A-4E, for example.

The following illustrative embodiments are explained in terms of operational circuitry. The operational circuitry may be configured to include such controllers, microcontrollers, logic devices, memory, and the like, as selected, needed, or desired, for performing the method steps for which each is adapted and configured.

An illustrative embodiment of the present invention includes an implantable cardioverter/defibrillator comprising a lead electrode assembly including a number of electrodes, and a canister housing operational circuitry, wherein the lead electrode assembly is coupled to the canister. In the illustrative embodiment, the operational circuitry is configured to analyze cardiac events using a template having a template data set and template parameters, and the operational circuitry is configured to perform the steps of: capturing a signal using electrodes implanted in a patient's torso; configuring the captured signal in accordance with the template parameters; aligning the template data set with the captured signal; and comparing the template data set to the captured signal.

In a further embodiment, the operational circuitry is further configured to perform the step of classifying the captured signal as being normal or abnormal. In another embodiment, the operational circuitry is configured such that the template parameters include a manner of selecting a fiducial point for the template and the captured signal. In yet another embodiment, the operational circuitry is configured such that the template parameters include a manner of selecting data points around the fiducial point of the captured signal.

In another embodiment, the operational circuitry is further configured such that the template parameters include a manner of selecting data points to form a template window. For another embodiment, the operational circuitry is further configured for performing the step of capturing a signal using subcutaneously implanted electrodes. In yet another embodiment, the operational circuitry is further configured such that: the template includes a fiducial point within the template data set defined by the template parameters; the template data set includes begin and end points relative the fiducial point, the placement of the begin and end points being defined by the template parameters; and the step of configuring the captured signal comprises: selecting a fiducial point in the captured signal; and identifying beginning and ending points of the captured signal according to the placement of the begin and end points of the template data set.

In yet another apparatus embodiment, the operational circuitry is further configured such that the step of comparing the template data set to the captured signal includes performing a correlation waveform analysis between the captured signal defined between its beginning and ending points, and the template data set. The operational circuitry may include a microcontroller. In another embodiment, the operational circuitry includes readable media including an instruction set for performing the capturing, configuring, aligning and comparing steps.

An embodiment of the present invention may include an implantable cardioverter/defibrillator comprising a lead electrode assembly including a number of electrodes, and a canister housing operational circuitry, wherein: the lead electrode assembly is coupled to the canister; the operational circuitry is configured to analyze cardiac events using a template having a template data set and template parameters; and the operational circuitry is configured to perform a number of steps. In the illustrative embodiment, the steps may include, for a number of selected captured cardiac signals, the steps of: configuring the captured signal in accordance with the template parameters, aligning the template data set with the captured signal, and comparing the template data set to the captured signal. The operational circuitry may be further configured for tracking the number of normal and abnormal captured signals, and determining whether therapy is indicated.

In a further embodiment, the operational circuitry is further configured such that the configuring step includes identifying a fiducial point in the selected captured cardiac signals. In another embodiment, the operational circuitry is further configured to perform the steps of: capturing a number of cardiac signals; analyzing the individual captured cardiac signals to determine whether the captured cardiac signals likely represent a cardiac event; and selecting those individual captured cardiac signals which likely represent a cardiac event.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An implantable defibrillator comprising:
   a lead electrode assembly including a number of electrodes; and
   a canister housing operational circuitry;
   wherein:
   the lead electrode assembly is coupled to the canister;
   the operational circuitry is configured to analyze cardiac events using a template having a template data set and template parameters, the template parameters including definition of an amplitude peak of the template data set as a fiducial point and start and end points surrounding the fiducial point; and
   the operational circuitry is configured to perform the steps of:
   capturing a signal using electrodes implanted in a patient's torso;

configuring the captured signal in accordance with the template parameters, including defining a signal fiducial point in the captured signal, wherein the captured signal includes a plurality of signal samples and the signal fiducial point is set as a peak signal sample;

aligning the template data set with the configured captured signal using the template and signal fiducial points; and comparing the aligned template data set to the signal samples in the configured captured signal, including comparing the template fiducial point to the sample fiducial point.

2. The implantable defibrillator of claim 1, wherein the operational circuitry is further configured to perform the step of classifying the captured signal as being normal or abnormal such that:

if the configured captured signal correlates to the aligned template data set, the operational circuitry classifies the captured signal as being normal; or if the configured captured signal poorly correlates to the aligned template data set, the operational circuitry classifies the captured signal as being abnormal.

3. The implantable defibrillator of claim 2, wherein the operational circuitry is further configured such that the configured captured signal, if determined to be normal, represents a portion of a single cardiac beat including an R-wave.

4. The implantable defibrillator of claim 2 wherein the operational circuitry is configured to:

track the number of normal and abnormal captured signals;

determine whether therapy is indicated using the number of normal and abnormal captured signals; and if therapy is indicated, deliver therapy.

5. The implantable defibrillator of claim 1, wherein the operational circuitry is further configured such that the template parameters include a manner of selecting data points to form a template window.

6. The implantable defibrillator of claim 1, wherein the operational circuitry is further configured for performing the step of capturing a signal using only subcutaneously implanted electrodes.

7. The implantable defibrillator of claim 1, wherein the operational circuitry is further configured such that the step of comparing the aligned template data set to the configured captured signal includes performing a correlation waveform analysis between the configured captured signal defined between its beginning and ending points, and the aligned template data set.

8. The implantable defibrillator of claim 1, wherein the operational circuitry includes a microcontroller.

9. The implantable defibrillator of claim 1, wherein the operational circuitry includes readable media including an instruction set for performing the capturing, configuring, aligning and comparing steps.

10. The implantable defibrillator of claim 1, wherein the operational circuitry is further configured such that the configured captured signal includes a plurality of amplitude samples, and the comparing step includes comparing amplitudes of samples from the configured captured signal to stored amplitudes for the aligned template data set.

11. The implantable defibrillator of claim 1, wherein the operational circuitry is further configured such that the comparing step includes performing a correlation waveform analysis between the configured captured signal and the aligned template data set.

12. The implantable defibrillator of claim 1 wherein the operational circuitry is configured such that:

the template data set comprises a set of i time-ordered samples $\{T0 \ldots Ti\}$ of electrical cardiac signals, with a sample, $Tf$, of the template data set being identified as a highest amplitude or magnitude signal in the template data set and serving as a fiducial point and with a first set of samples $\{T0 \ldots Tf-1\}$ and a second set of samples $\{Tf+1 \ldots Ti\}$ being identified as belonging to a sample window for the template data set;

the step of configuring the captured signal in accordance with the template parameters comprises identifying a sample within a series of sampled signals as a fiducial point, $Sf$, that has a highest relative amplitude within a set of such sampled signals, and selecting a set of time-ordered samples around $Sf$ including $\{S0 \ldots Sf-1\}$ and $\{Sf+1 \ldots Si\}$ according to the sample window of the template data set;

the step of aligning the template data set with the captured signal includes aligning time ordered signal samples $\{S0 \ldots Si\}$ with time ordered template samples $\{T0 \ldots Ti\}$ using the fiducial points $\{Sf, Tf\}$; and the step of comparing the aligned template data set to the configured captured signal includes performing correlation analysis of the amplitudes of the aligned data sets $\{S0 \ldots Si\}$ and $\{T0 \ldots Ti\}$.

13. The implantable defibrillator of claim 1 wherein the operational circuitry is configured such that:

the template parameters include one or more size parameters indicating how many samples are part of the template, and one or more position parameters indicating a position of a fiducial point in the template; and the step of configuring the captured signal in accordance with the template parameters includes identifying a fiducial point in the captured signal, and defining a signal window around the fiducial point using the one or more size parameters and the one or more position parameters.

14. The implantable defibrillator of claim 1 wherein the operational circuitry is also configured to:

track the number of normal and abnormal captured signals;

determine whether therapy is indicated using the number of normal and abnormal captured signals; and if therapy is indicated, deliver therapy.

15. An implantable defibrillator comprising a canister and a lead electrode assembly, the lead electrode assembly being coupled to the canister, with operational circuitry disposed in the canister for performing cardiac signal analysis and delivering electrical cardiac stimulus using a plurality of electrodes disposed on the canister and lead electrode assembly, wherein the operational circuitry is configured such that it performs a method comprising:

capturing electrical cardiac signals;

storing a template comprising template data and template parameters, the template data including a number of sample values disposed about a fiducial point, the template parameters indicating a number of data points in the template and a relative location of the fiducial point within the number of data points;

configuring a captured electrical cardiac signal using the template parameters such that a signal fiducial point of the captured electrical cardiac signal is defined with a predetermined number of samples on either side of the signal fiducial point;

calculating a correlation of the configured captured electrical cardiac signal to the template data by aligning the template data fiducial point with the signal fiducial point and comparing the template data including the template data fiducial point to the configured captured electrical cardiac signal including the signal fiducial point;

using the calculated correlation to determine whether the captured electrical cardiac signal is normal or abnormal;

tracking the number of normal and abnormal captured signals;

determining whether therapy is indicated using the number of normal and abnormal captured signals; and if therapy is indicated, delivering therapy;

wherein the template fiducial point is defined by identifying an amplitude or magnitude peak of the template data, and the signal fiducial point is defined by identifying an amplitude or magnitude peak of the signal data.

16. The implantable defibrillator of claim 15 wherein the operational circuitry comprises a microcontroller configured to control the operation of steps of capturing electrical cardiac signals, storing a template, configuring a captured electrical cardiac signal, calculating a correlation and using the calculated correlation to determine whether the captured electrical cardiac signal is normal or abnormal.

17. The implantable defibrillator of claim 15 wherein:

the stored template comprises a series of time ordered samples in which the fiducial point resides with a plurality of values preceding and following the fiducial point in the template, wherein the fiducial point occurs at a peak of the series of time ordered samples; and the captured electrical cardiac signal is configured to as a signal window comprising a series of time ordered signal samples within which the signal fiducial point is a signal fiducial point represents a peak within the series of time ordered signal samples.

18. A method of cardiac signal analysis comprising:

an implanted defibrillator capturing a cardiac electrical signal;

the implanted defibrillator comparing the cardiac electrical signal to a first stored template having first template parameters including a first template fiducial point definition and first template window definition predetermining a number of samples before and after the first template fiducial point that form the first template, the step of comparing the cardiac electrical signal to the first stored template including defining a first signal fiducial point in the cardiac electrical signal, a first start point and a first end point for the cardiac electrical signal and using the first signal fiducial point and first template fiducial point to align the template to the cardiac electrical signal and using the first template window definition to determine how much of the cardiac electrical signal to compare to the first template;

the implanted defibrillator comparing the cardiac electrical signal to a second stored template having second template parameters including a second template fiducial point definition and second template window definition predetermining a number of samples before and after the second template fiducial point that form the second template, the step of comparing the cardiac electrical signal to the second stored template including defining a second signal fiducial point in the cardiac electrical signal and using the second signal fiducial point and second template fiducial point to align the template to the cardiac electrical signal and using the second template window definition to determine how much of the cardiac electrical signal to compare to the second template;

the implantable defibrillator using the results of comparison to the first and second stored templates to determine whether the cardiac electrical signal indicates malignant function of the patient's heart; and if the patient's heart function is malignant, the implantable defibrillator delivering stimulus to the patient;

wherein the first template window definition and the second template window definition are different from one another.

19. The method of claim 18 wherein the first stored template, first fiducial point, first start point and first end point are defined independently of the second stored template, second fiducial point, second start point and second end point.

* * * * *